United States Patent
Brown

[11] Patent Number: 5,135,620
[45] Date of Patent: Aug. 4, 1992

[54] SEPARATION OF ETHYLBENZENE FROM XYLENES BY EXTRACTIVE DISTILLATION

[75] Inventor: Ronald E. Brown, Bartlesville, Okla.

[73] Assignee: Phillips Petroleum Company, Bartlesville, Okla.

[21] Appl. No.: 754,867

[22] Filed: Sep. 4, 1991

[51] Int. Cl.$^5$ .............................. B01D 3/40
[52] U.S. Cl. ........................... 203/57; 203/60; 203/69; 203/98; 585/805; 585/849; 585/856; 585/867
[58] Field of Search ............ 203/57, 60, 61, 98, 203/69; 585/833, 856, 864, 849, 867, 866, 805

[56] References Cited

U.S. PATENT DOCUMENTS

| | | | |
|---|---|---|---|
| 2,532,031 | 11/1950 | Nixon et al. | 203/50 |
| 2,739,992 | 3/1956 | Lien et al. | 585/834 |
| 2,848,518 | 8/1958 | Fragen | 585/805 |
| 3,105,017 | 9/1963 | Amir et al. | 203/67 |
| 3,356,593 | 12/1967 | Suzuki | 203/51 |
| 3,401,112 | 9/1968 | Dunlop et al. | 585/848 |
| 3,624,172 | 11/1971 | Adams | 585/478 |
| 3,634,530 | 1/1972 | Bills | 585/484 |
| 4,025,574 | 5/1977 | Tabler et al. | 585/848 |
| 4,129,605 | 12/1978 | Tabler et al. | 585/259 |
| 4,141,925 | 2/1979 | Pavlov et al. | 203/51 |
| 4,292,142 | 9/1981 | Berg | 203/51 |
| 4,299,668 | 11/1981 | Berg | 203/51 |
| 4,398,052 | 8/1983 | Tabler et al. | 585/845 |
| 4,400,564 | 8/1983 | Johnson et al. | 585/845 |

FOREIGN PATENT DOCUMENTS 0507549  5/1976  U.S.S.R. .................... 203/57

Primary Examiner—Virginia Manoharan
Attorney, Agent, or Firm—K. K. Brandes

[57] ABSTRACT

Ethylbenzene is separated from xylene(s) by extractive distillation employing at least one copper(I) salt of a hydrocarbonsulfonic acid as extractant(s).

18 Claims, 1 Drawing Sheet

SEPARATION OF ETHYLBENZENE FROM XYLENES BY EXTRACTIVE DISTILLATION

BACKGROUND OF THE INVENTION

This invention relates to the separation of ethylbenzene from xylenes by extractive distillation.

Extractive distillation is a well known technique for separating mixtures of components having a relative volatility close to unity (i.e., having nearly equal volatility and having nearly the same boiling point). It is difficult to separate the components of such mixtures by conventional fractional distillation. In extractive distillation, an entrainer (also called solvent or extractant) is introduced into a distillation column above the entry point of the feed mixture which is to be separated. The entrainer affects the volatility of the higher boiling feed component(s) sufficiently to facilitate the separation of the various feed components by distillation and exits with the bottoms fraction, as has been described in the article entitled "Extractive Distillation Saves Energy" by Ian Sucksmith, Chemical Engineering, Jun. 28, 1982, pages 91-95. Other literature sources on extractive distillation techniques include the "Handbook of Separation Techniques for Chemical Engineers" by Philip A. Schweitzer, McGraw-Hill Book Company, 1979, pages 1-135 to 1-143; and Perry's Chemical Engineers Handbook, 6th Edition, McGraw-Hill Book Company 1984, pages 13-53 to 13-57.

Even though extractive distillation processes for separating ethylbenzene from xylenes are known and have been described in the patent literature, e.g., in U.S. Pat. Nos. 4,299,668, 4,292,142, 3,105,017 and 2,532,031, there is still a need for developing novel effective entrainers for the extractive distillation of ethylbenzene/xylene mixtures.

SUMMARY OF THE INVENTION

It is an object of the invention to provide a process for separating ethylbenzene from xylene(s) by extractive distillation employing a selective entrainer (also referred to as extractant or solvent). Other objects and advantages will be apparent from the detailed description of the invention and the appended claims.

In accordance with this invention, in a process for separating ethylbenzene from at least one xylene contained in a feed mixture by extractive distillation, the improvement comprises employing as entrainer at least one copper(I) salt of a hydrocarbonsulfonic acid.

DETAILED DESCRIPTION OF THE INVENTION

Figure 1:
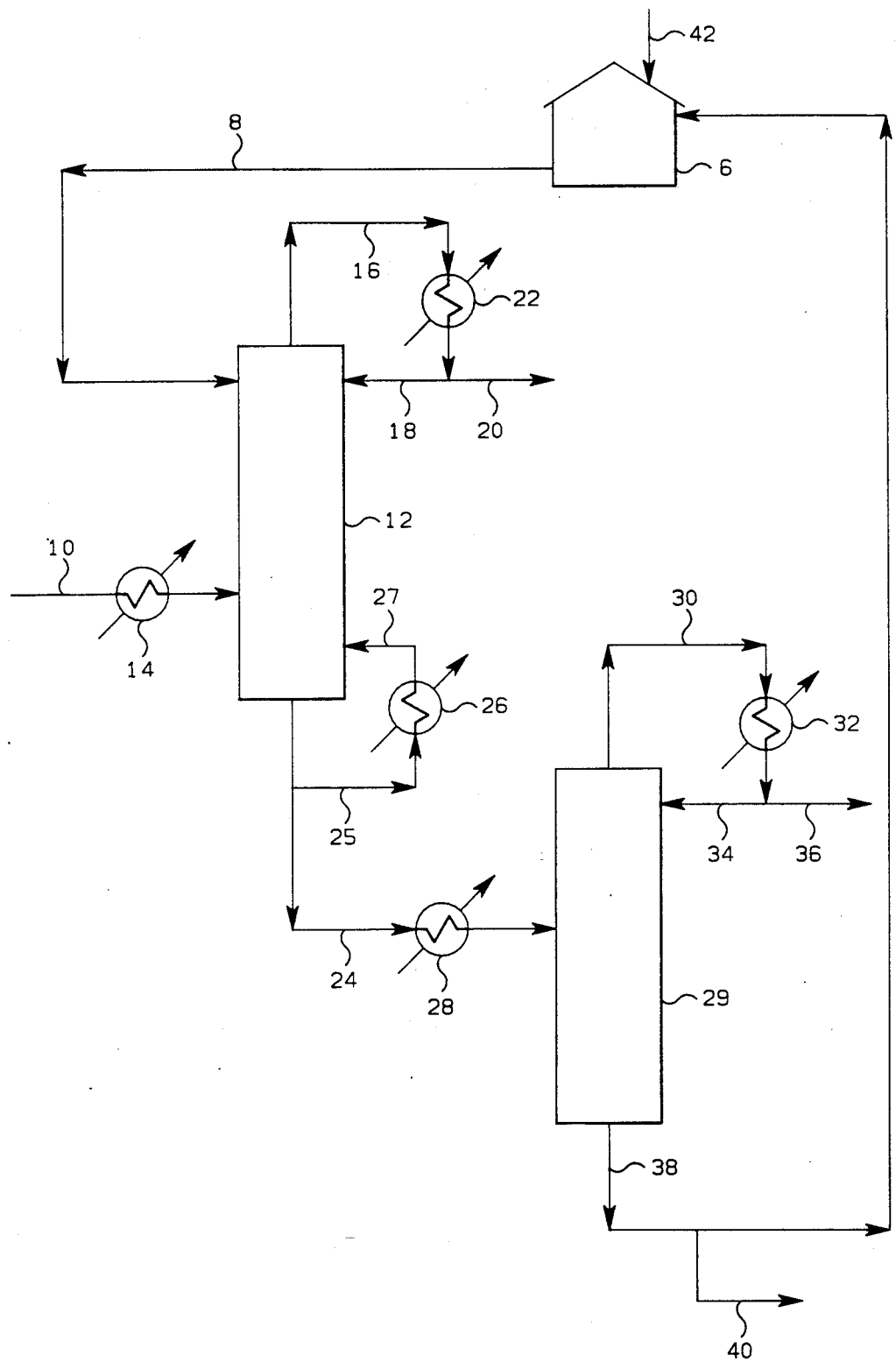
FIG. 1 illustrates the extractive distillation process of this invention.

In an extractive distillation process, an agent (called "entrainer" or "extractant" or "solvent") is added to a feed mixture of components to be separated so that the relative volatilities of the components of the mixture are changed such that a sufficient difference in volatility of the components results and effective separation by distillation becomes possible. The added entrainer is usually chosen so as to exhibit high "selectivity" regarding the components to be separated. Selectivity is a term related to the change in volatilities of components in the mixture caused by the presence of the solvent. The larger the difference in relative volatility of the components in the mixture, the easier the separation of the components by fractional distillation becomes. Therefore, an entrainer of high selectivity is one which causes great differences between the relative volatilities of the components in a mixture, and will allow for the separation of components in a mixture with fewer distillation stages, lower amount of reflux and higher product purity.

In the process of this invention, any hydrocarbon-containing feed which comprises (preferably consists essentially of a mixture of) ethylbenzene and at least one xylene (i.e., ortho- or meta- or para-xylene or mixtures of two or three of these xylene isomers) can be used in the extractive distillation process of this invention. Preferably, the ethylbenzene content in the feed is about 5-95 weight-% (more preferably about 20-80 weight-%), and the xylene content is about 5-95 weight-% (more preferably about 20-80 weight-%). When more than one xylene is present in the feed, the various xylene isomers can be present at any weight ratio.

Any suitable copper (I) salt of a hydrocarbonsulfonic acid can be employed as entrainer. Preferred hydrocarbon sulfonic acids are those disclosed in U.S. Pat. No. 4,400,564 and include alkanesulfonic acids containing 4-20 carbon atoms per molecule and aromatic sulfonic acids containing 6-22 carbon atoms per molecule.

The alkanesulfonic acids useful in the practice of this invention can be straight chain or branched. Non-limiting examples of suitable alkanesulfonic acids include n-butanesulfonic acid, 2-ethyl-1-hexanesulfonic acid, 2-methylnonanesulfonic acid, dodecanesulfonic acid, 2-ethyl-5-n-octyldecanesulfonic acid, n-eicosanesulfonic acid, and mixtures thereof.

Non-limiting examples of aromatic sulfonic acids useful in the practice of this invention include benzenesulfonic acid, alkylbenzenesulfonic acids wherein the alkyl member contains from 1 to 10 carbon atoms, such as p-toluenesulfonic acid, p-dodecylbenzenesulfonic acid, p-hexadecylbenzenesulfonic acid, and the like, naphthalenesulfonic acid, phenolsulfonic acid, naphtholsulfonic acids and halogenbenzenesulfonic acids, such as p-chlorobenzenesulfonic acid, p-bromobenzenesulfonic acid, and mixtures thereof. A presently preferred aromatic sulfonic acid is p-dodecylbenzenesulfonic acid. Commercially available mixtures of o-, m-, and p-dodecylbenzenesulfonic acid can be employed. Preferably, the mixture employed is predominantly (i.e., 84-90 mole percent) the para isomer.

Petroleum sulfonic acids which comprise various alkane sulfonic acids and aromatic sulfonic acids can also be used in the practice of this invention. Such petroleum sulfonic acids can be prepared by sulfonation, generally with an $SO_3/SO_2$ mixture, of a deasphalted solvent-refined petroleum fraction having a viscosity of about 140-720 SUS at 210° F.

The preferred copper salts used as sorbents in the present invention are generally prepared by refluxing a solution of the sulfonic acid in a suitable diluent, preferably xylene(s), together with cuprous oxide, with a provision for removing the water of reaction, as has been described in U.S. Pat. No. 4,400,564. The preparation is generally carried out in an oxygen-free inert atmosphere, such as under nitrogen, preferably at a molar ratio of sulfonic acid to copper of about 1:1, for a period of time sufficient to substantially complete the reaction. If desired, the formed copper salt can be separated from the diluent, such as by vacuum distillation.

The copper(I) sulfonate entrainer can be added to the distillation column in solid form. But this procedure is presently not preferred. Generally, the copper(I) sulfonate is dissolved in a suitable hydrocarbon solvent, preferably a aromatic hydrocarbon solvent containing 6-15 carbon atoms per molecule to produce a solution of the entrainer material. Examples of suitable aromatic solvents include benzene, the alkyl derivatives of benzene, such as toluene, xylene isomers, isopropylbenzene, 1,3,5-trimethylbenzene, hexamethylbenzene, halogen-substituted benzenes, polynuclear aromatic hydrocarbons such as naphthalene, methylnaphthalenes and the like. It is also possible to employ an aromatic hydrocarbon containing mixture, such as light cycle oil, as solvent. The aromatic solvents which are presently more preferred are xylene(s), i.e., ortho- or meta- or para-xylene, or a mixture of two or three xylenes (at any suitable ratio). Generally, the concentration of the dissolved copper(I) sulfonate(s) in the entrainer solution is about 0.05-2 mole/l, preferably about 0.2-1.5 mole/l.

Any suitable weight ratio of Cu(I) hydrocarbonsulfonate(s) to the feed can be employed. This weight ratio generally is in the range of about 0.02:1 to about 10:1, preferably in the range of about 0.1:1 to about 2:1. Any suitable reflux ratio (i.e., the weight ratio of the portion of condensed vapor which is returned to the distillation column to the portion of condensed vapor which is withdrawn as distillate product) can be employed in the extractive distillation process of this invention. Generally the reflux ratio is in the range of from about 0.1:1 to about 100:1, preferably in the range of from about 0.5:1 to about 30:1.

Any suitable feed entry location can be selected. Generally the feed entry location is in the range of from about 2 to about 70 percent of the total height of the packed or trayed column, measured upward from the bottom of the column, preferably in the range of from about 5 to about 60 percent, more preferably in the range of from about 7 to about 70 percent.

Any suitable entrainer entry location can be selected. Generally the entrainer entry location is in the range of from about 50 to about 99 percent of the total height of the packed or trayed column (i.e., within the upper half of the column), preferably in the range of from about 70 to about 99 percent, more preferably in the range of from about 80 to about 99 percent.

Any suitable temperature in the reboiler vessel (containing primarily the higher boiling feed components and the solvent) can be employed. The temperature is generally in the range of from about 250° to about 550° F., preferably in the range of from about 300° to about 500° F. The extractive distillation column is generally heated (more near the bottom, and less near the top). Generally, the temperature at the top of the column where the vapor exits into the condenser is in the range of from about 150° to about 500° F., preferably in the range of from about 250° to about 400° F. Entrainer and feed are generally preheated (generally to a temperature close to the column temperature of the corresponding entry point) before they are introduced into the column. Any suitable pressure can be employed during the extractive distillation. Generally the pressure is about 5 to about 100 psig, preferably about 8 to about 20 psig.

The overhead distillate product (withdrawn from the top of the column) generally contains a smaller volume percentage of the xylene(s) than the feed and a larger volume percentage of ethylbenzene than the feed. The bottoms product (a portion of which can be reheated and recycled to the lower portion of the column) contains a larger volume percentage of xylene(s) than the feed and a smaller volume percentage of the ethylbenzene than the feed. Furthermore, the bottoms product contains the added entrainer, which can be separated from the larger portion of xylene(s) by distillation or other suitable separating means and can then be recycled as a solution of the entrainer in xylene(s) to the extractive distillation column. Thus, the solvent for the entrainer is essentially the same as the desired bottoms product, namely xylene(s).

Any suitable total column height, packed column height, column diameter and number of trays in the extraction distillation column can be employed. The exact dimensions and column designs depend on the scale of the operation, the exact feed composition, the exact solvent composition, the desired recovery and degree of purity of the various product, and the like, and can be determined by those having ordinary skills in the art.

The invention can be better understood by reference to FIG. 1 and the following description of a preferred embodiment of the invention. The feed mixture comprising ethylbenzene and xylene(s) is introduced through conduit 10 to a fractionation zone such as multi-stage distillation column 12. The temperature of the feed mixture flowing through conduit 10 can be adjusted as needed by controlling heat exchanger 14 so as to add heat to or remove heat from the feed mixture. Entrainer from entrainer storage 6 is introduced to distillation column 12 through conduit 8, and an overhead stream enriched in ethylbenzene is withdrawn from an upper portion of distillation column 12 through conduit 16. This overhead stream can be completely passed to storage or to other processing units or, as is often the case, the overhead stream can be partially or totally condensed, with a portion thereof being returned to the fractionation zone as reflux. The overhead stream passing through conduit 16 is condensed in condenser 22 to yield a condensed overhead stream. A portion of the condensed overhead stream can be returned to distillation column 12 as reflux through conduit 18, while the remainder of the condensed overhead stream (generally consisting essentially of ethylbenzene) is yielded as product or passed to other processing units through conduit 20.

A bottoms stream is withdrawn from a lower portion of the fractionation zone represented by distillation column 12 through conduit 24. A portion of the fluids withdrawn from the bottom of distillation column 12 may be heated and returned to distillation column 12. For example, a portion of the bottoms product stream can be withdrawn through conduit 25, heated in reboiler 26 and then passed back to a lower portion of distillation column 12 through conduit 27.

Operating conditions in heat exchanger 14, condenser 22 and reboiler 26 can be controlled and interfaced with entrainer flow through conduit 8, feed mixture flow through conduit 10, reflux flow through conduit 18 and bottoms stream flow through conduit 24 such that the feed mixture introduced into distillation column 12 will be fractionated to yield an overhead stream which is enriched in ethylbenzene and a bottoms stream predominantly comprising xylene(s) and the entrainer.

The bottoms stream passing through conduit 24 can be passed to storage, used in other processes or, preferably, passed to another fractionation zone, such as distillation column 29. Any adjustments to the temperature of the bottoms stream passing through conduit 24 necessary for efficient fractionation in distillation column 29 can be made by appropriately adjusting heat exchanger 28. An overhead stream predominantly comprising xylene(s) is withdrawn from an upper portion of distillation column 29 through conduit 30. This overhead stream can be at least partially condensed in condenser 32. A portion of the overhead stream withdrawn from condenser 32 can be returned through conduit 34 as reflux for distillation column 29, with the remainder of the overhead stream being withdrawn as product, i.e., xylene(s) of high purity (preferably higher than 95%), through conduit 36.

A bottoms stream predominantly comprising the entrainer solution, i.e., at least one copper(I) salt of a hydrocarbonsulfonic acid dissolved in xylene(s), is withdrawn from a lower portion of distillation column 29 through conduit 38. A portion of this bottoms stream is preferably routed back to entrainer storage 6 and then recycled to distillation column 12, while another portion of the bottoms stream is heated in a reboiler (not shown) and returned to the lower portion of column 29. From time to time, impurities which may build up in the entrainer can be removed from the system by removing a small purge stream through conduit 40. Entrainer lost through the purge stream or through other processing losses may be made up by a makeup stream passing through conduit 42 and into entrainer storage 6.

The following example is presented to further illustrate the invention and is not to be considered unduly limiting the scope of this invention.

EXAMPLE

This example illustrates the use of a solution of a Cu(I) hydrocarbonsulfonate as the entrainer in the extractive distillation of a feed containing ethylbenzene and xylene(s).

To a hydrocarbon mixture of 21 weight-% ethylbenzene and 79 weight-% of a mixture of para-, meta- and ortho-xylenes was added a 1 molar solution of Cu(I) dodecylbenzenesulfonate in xylenes as entrainer. The total mixture (including the entrainer) was heated in a constant temperature bath to a temperature near the boiling point of the feed, and the vapor was circulated in a Jurgenson equilibrium cell for about 20-30 minutes until equilibrium conditions were attained, i.e., until the pressure in the cell remained constant. Then a small sample was withdrawn by means of a sample bomb from the cell containing the liquid phase of the equilibrium system, and a sample of the vapor was withdrawn by means of a sample bomb just above the cell. Both samples were analyzed, and the mole fractions of ethylbenzene and xylenes in the liquid phase and in the vapor phase were determined by means of a gas chromatograph. The relative volatility R was calculated as follows:

$$R = \frac{Y1/Y2}{X1/X2} = \frac{Y1/X1}{Y2/X2},$$

wherein Y1 and Y2 are the mole fractions of ethylbenzene and xylenes, respectively, in the vapor phase; and X1 and X2 are the mole fractions of ethylbenzene and xylenes, respectively, in the liquid phase. Test results are summarized in Table I.

TABLE I

| Entrainer:Feed Weight Ratio[1] | Relative Volatility R |
|---|---|
| 0 | 1.04 |
| 0.5:1 | 1.16 |

[1]expressed as weight ratio of Cu⁺ contained in entrainer to the ethylbenzene/xylene feed.

Based on the test results in Table I, it is concluded that Cu(I) hydrocarbonsulfonates will be effective as entrainers in the extractive distillation of feeds containing ethylbenzene and xylenes.

Reasonable variations, modifications and adaptations for various usages and conditions can be made within the scope of the disclosure and the appended claims, without departing from the scope of this invention.

That which is claimed is:

1. A process for separating ethylbenzene from at least one xylene selected from the group consisting of ortho-xylene, meta-xylene and para-xylene contained in a feed, said process consisting essentially of subjecting said feed to extractive distillation and employing an extractant consisting essentially of at least one dissolved copper(I) salt of a hydrocarbonsulfonic acid;

wherein said process produces (i) an overhead product which contains a larger volume percentage of ethylbenzene and a smaller volume percentage of said at least one xylene than said feed, and (ii) a bottoms product which contains said extractant and a larger volume percentage of said at least one xylene and a smaller volume percentage of ethylbenzene than said feed.

2. The process in accordance with claim 1, wherein the content of ethylbenzene in said feed is about 5-95 weight-% and the content of said at least one xylene in said feed is about 5-95 weight-%.

3. The process in accordance with claim 1, wherein the weight ratio of said extractant to said feed is in the range of about 0.02:1 to about 10:1.

4. The process in accordance with claim 3, wherein said weight ratio is in the range of about 0.1:1 to about 2:1.

5. The process in accordance with claim 1, further consisting essentially of the step of at least partially separating said at least one xylene from said extractant contained in said bottoms product.

6. The process in accordance with claim 5, further consisting essentially of the step of recycling said extractant.

7. The process in accordance with claim 1, wherein said at least one copper(I) salt of a hydrocarbonsulfonic acid is at least one copper(I) salt of an alkanesulfonic acid containing 4-20 carbon atoms per molecule.

8. The process in accordance with claim 7, wherein said alkane sulfonic acid is selected from the group consisting of n-butanesulfonic acid, 2-ethyl-1-hexanesulfonic acid, 2-methylnonanesulfonic acid, dodecanesulfonic acid, 2-ethyl-5-n-octyldecanesulfonic acid and n-eicosanesulfonic acid.

9. The process in accordance with claim 1, wherein said at least one copper(I) salt of a hydrocarbonsulfonic acid is at least on copper(I) salt of an aromatic sulfonic acid containing 6-22 carbon atoms per molecule.

10. The process in accordance with claim 9, wherein said at least one copper(I) salt of an aromatic sulfonic acid is dissolved in an aromatic hydrocarbon solvent so as to form a solution.

11. A process in accordance with claim 10, wherein the solution of said at least one copper(I) salt of an aromatic sulfonic acid in said aromatic hydrocarbon solvent has a concentration of about 0.05-2 mole/l.

12. A process in accordance with claim 11, wherein said at least one copper(I) salt of an aromatic sulfonic acid is copper(I) p-dodecylbenzenesulfonate.

13. The process in accordance with claim 12, wherein said copper(I) p-dodecylbenzenesulfonate is dissolved in xylene solvent.

14. The process in accordance with claim 9, wherein said aromatic sulfonic acid is benzenesulfonic acid.

15. The process in accordance with claim 9, wherein said aromatic sulfonic acid is at least one alkylbenzenesulfonic acid wherein the alkyl member contains 1 to 10 carbon atoms.

16. The process in accordance with claim 9, wherein said aromatic sulfonic acid is naphthalenesulfonic acid.

17. A process in accordance with claim 1, wherein the reflux ratio in said extractive distillation is in the range of about 0.1:1 to about 100:1.

18. The process in accordance with claim 1, wherein said feed consists essentially of ethylbenzene and said at least one xylene.

* * * * *